United States Patent [19]

Strauss

[11] Patent Number: 5,802,865
[45] Date of Patent: Sep. 8, 1998

[54] EVAPORATIVE PERSONAL COOLER

[75] Inventor: Ted N. Strauss, Fairfax, Calif.

[73] Assignee: The Sharper Image, San Francisco, Calif.

[21] Appl. No.: 924,580

[22] Filed: Sep. 5, 1997

[51] Int. Cl.[6] .............................. F25D 5/00; F25D 23/12
[52] U.S. Cl. ............................................ 62/259.3; 62/314
[58] Field of Search .................................... 62/259.3, 304, 62/314, 121; 2/458, DIG. 1, DIG. 11

[56] References Cited

U.S. PATENT DOCUMENTS

| | | |
|---|---|---|
| 1,633,586 | 6/1927 | Hunter . |
| 1,907,709 | 5/1933 | Barrow . |
| 2,160,567 | 5/1939 | Stern ........................................... 2/171 |
| 2,223,332 | 11/1940 | Sterne ......................................... 2/171 |
| 2,783,474 | 3/1957 | Campagna et al. .......................... 2/171 |
| 2,832,077 | 4/1958 | McGinnis .................................... 2/171 |
| 3,029,438 | 4/1962 | Henschel .......................................... 2/7 |
| 3,096,702 | 7/1963 | Malone et al. .......................... 63/259.3 |
| 3,296,819 | 1/1967 | Gough ........................................ 62/259 |
| 3,429,138 | 2/1969 | Goldmerstein ............................ 62/259 |
| 3,466,664 | 9/1969 | Militello ..................................... 2/171 |
| 3,610,323 | 10/1971 | Troyer ....................................... 165/46 |
| 4,130,902 | 12/1978 | Mackenroth, III et al. ................... 2/7 |
| 4,742,581 | 5/1988 | Rosenthal ................................... 2/181 |
| 4,893,356 | 1/1990 | Waters ..................................... 2/171.3 |
| 5,146,765 | 9/1992 | Waters ................................... 62/259.3 |
| 5,175,887 | 1/1993 | Kim ............................................ 2/174 |
| 5,564,124 | 10/1996 | Elsherif et al. ............................... 2/69 |

*Primary Examiner*—William Doerrler
*Attorney, Agent, or Firm*—Flehr Hohbach Test Albritton & Herbert LLP

[57] ABSTRACT

A self-contained evaporative personal cooling device has an articulated C-shaped housing that fits conformally around a user's neck or forehead. The housing retains and urges at least one heat dissipating plate conformally against the user's neck or forehead. A sponge material within the housing contacts upper and/or lower portions of the metal plates but is spaced-apart from the plate to form a plenum. In use, the sponge material is saturated with water introduced through slots in the housing. A DC powered fan within the device draws air into the housing and circulates the air within the plenum and out through exit openings in the sponge material and housing. Moisture from the sponge material wets the plenum-facing surface of the metal plates, which surface preferably has been treated with a wicking material. Fan-circulated air promotes evaporation and heat is withdrawn by the plates from the user's neck or forehead, thus cooling the user.

20 Claims, 4 Drawing Sheets

EVAPORATIVE PERSONAL COOLER

FIELD OF THE INVENTION

The present invention relates generally to personal cooling devices, and more particularly to evaporative coolers that are worn around the neck or head of a user.

BACKGROUND OF THE INVENTION

Individuals often wish to be cooled, especially in warm ambient temperatures. The desire to be cooled may arise indoors or out, while exercising, engaging in sports, driving, or being in an environment that is not comfortably cool.

It is known in the art to provide a cap to be worn by an individual that can provide some cooling. U.S. Pat. No. 5,365,607 to Benevento, for example, discloses a cap whose headband includes a plurality of tapered porous pads. The pads are wet with water and apparently produce a cooling effect to the user's head as the water evaporates.

U.S. Pat. No. 3,029,438 to Henschel discloses a water-cooled cap in which an inner aluminum strip contacts the wearer's head, and is contacted with a water absorbent sponge strip (or strips), in turn over-covered by a fabric. The sponge material is wet, and as the water evaporates, the aluminum strip cools, thus cooling the wear's head.

U.S. Pat. No. 4,130,902 to Mackenroth discloses a cooling hat band that includes an outer support band, an inner absorbent band, a wicking element and a water reservoir. Reservoir water moves along the wicking element to the absorbent band, whence it evaporates, passing through holes in the support band. The evaporative effect is said to remove heat from the headband, and thus from the wear's forehead.

However, not all individuals like to wear caps, and participation in some sports, e.g. bicycling, may dictate that another type of headgear be worn, a helmet for example. Thus, several attempts have been made in the prior art to improve upon a basic cooling band, such as a tennis player might wear around the forehead. For example, U.S. Pat. No. 4,742,581 to Rosenthal discloses a laminated cooling band comprising a skin-contacting air pervious heat conductive layer edge-connected to an air pervious fabric that is moistened with water exposed to ambient air. This device is said to cool the wearer as water evaporates from the outer fabric. However, as is typical with many prior art devices, evaporative cooling is dependent upon ambient air motion. If the wearer is stationary, the efficiency of evaporative cooling decreases.

Notwithstanding the above devices, there is a need for a self-contained personal evaporative cooling device that promotes efficient cooling. If worn about the user's neck, such device should not require headgear. Further, such device should be useable on other portions of the user's body, the forehead, for example. Preferably such device should enhance evaporative cooling by maximizing the heat sinking area, maintaining a thin film of liquid upon such area, and by circulating air within the device. Such device should be simple to use and wear, and should provide cooling that lasts for several hours without replenishment of liquid or energizing source.

The present invention provides such a cooling device.

SUMMARY OF THE PRESENT INVENTION

The preferred embodiment of the present invention is a self-contained evaporative personal cooling device in the form of a C-shaped band that fits conformally around a portion of a user's body, e.g., the neck or forehead. The device includes an articulated housing within which is disposed a heat sinking or dissipating member, preferably implemented as a plurality of side-edge-joined metal plates that each have a first, neck-facing surface, and a second, opposite, surface. The metal plates are urged conformably against the user's neck or forehead such that the first, or exterior plate, surfaces contact the neck. A water-retaining preferably foam-like sponge material is disposed within the housing in contact with the upper and/or lower surfaces or regions of the metal plates but spaced-apart from the second surface of the plate body to form a plenum therebetween. The sponge material is saturated with a liquid, preferably water, introduced through liquid intake slots in the housing, before the cooling device is to be used. The device includes a DC powered fan that draws air into the housing though air intake vents and then circulates the air within the plenum defined between the metal plates and the sponge material and out through air exit vent openings in the housing. Moisture from the sponge material wets the plenum-facing surface of the metal plates, and the fan-circulated air produces evaporation. The evaporation cools the metal plates, which absorb heat from the user's neck or forehead and thus cools the user.

Preferably the plenum-facing surfaces of the metal plates define pins, ridges, fins, or the like to increase plate surface area. To help promote the cooling process, a wicking material is used to coat at least portions of the ridged contact surface area. During device manufacture a surfactant is applied to the sponge material and to the preferably wicked surface areas of the metal plates to encourage capillary-like liquid migration and promote cooling efficiency. In use, a wicking action encourages water migration from the sponge material to the ridge surfaces of the metal plates. Preferably the plenum-facing surface of the sponge material is covered with a moisture barrier. However the moisture barrier does not cover regions where the sponge material contacts the metal plates or where the sponge material is adjacent housing slits through which water is introduced. The barrier helps maximize evaporation at the metal plates by preventing circulation of dry plenum air from evaporating water from the foam. Further, the barrier reduces water loss and water leakage. If desired, a color-changing material may be included to serve as a low water indicator. To promote efficiency, the fan blade preferably includes a centermost axial portion that draws air into the housing through input vents, and an outermost radial portion that circulates the air in the plenum within the housing. Alternatively the fan might be replaced with other air-moving means including electro-kinetic mechanisms that move air silently and without moving parts.

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 1:
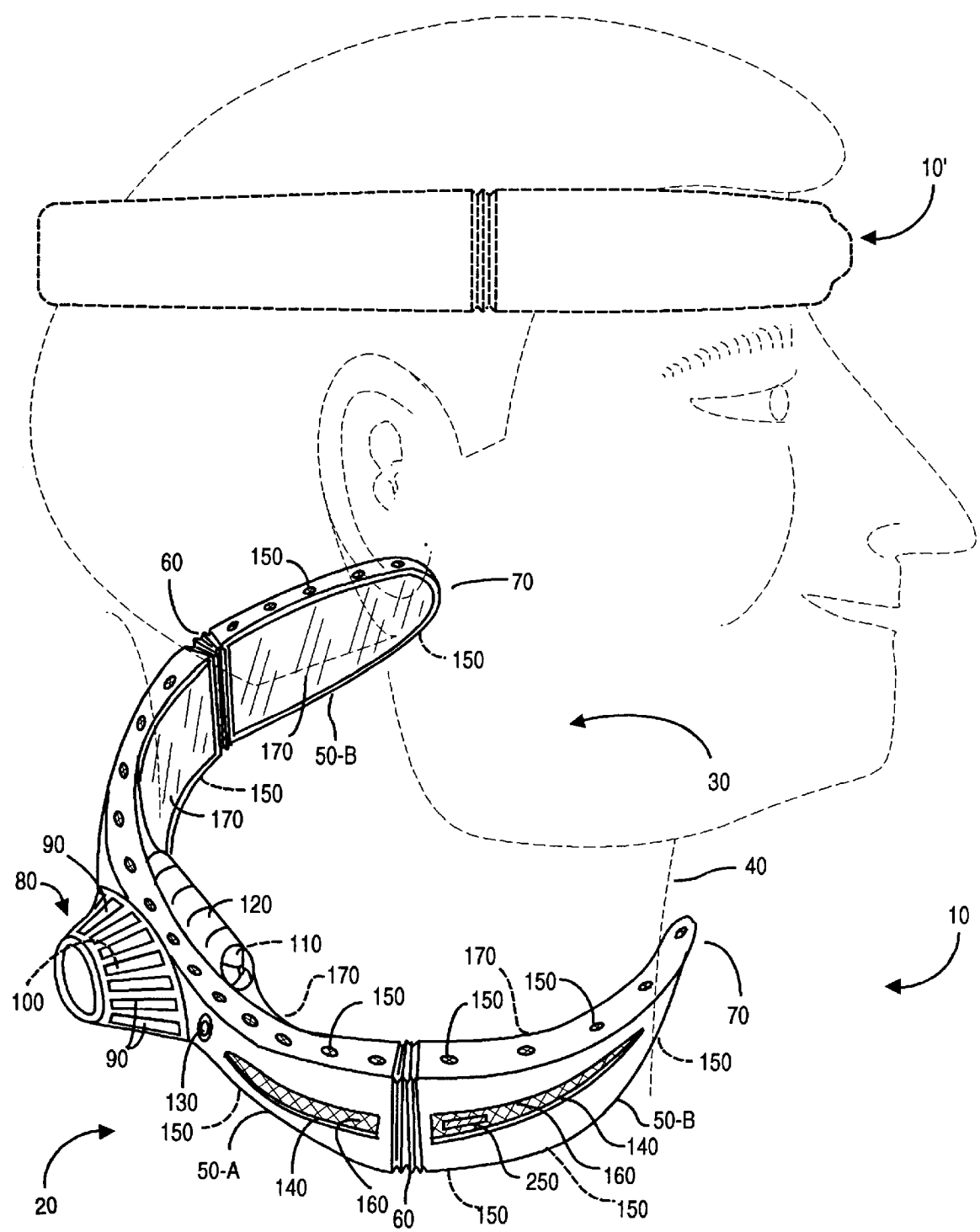
FIG. 1 is a perspective view of the present invention worn around the neck of a user.

FIG. 1 depicts an evaporative neck cooler 10 worn around the neck of a user, the user shown drawn in phantom lines. Alternatively, a cooler 10' may be worn in headband fashion around the forehead of a user, as shown in phantom. Hereinafter neck cooler 10 will be described, however it is to be understood that the description is also applicable to a forehead cooler 10'.

Figure 2:
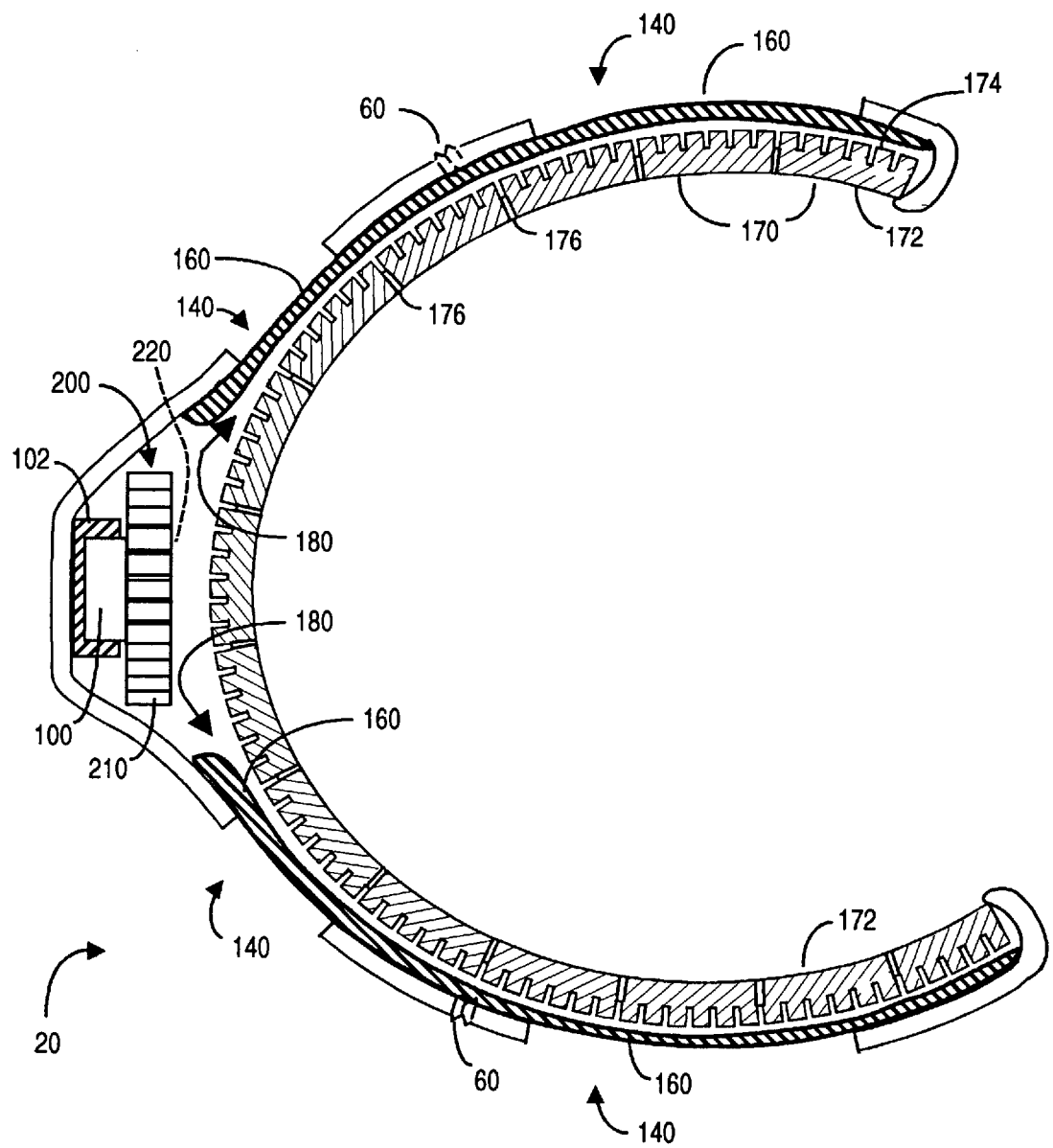
FIG. 2 is a cross-sectional view along the center of the present invention.

Cooler 10 includes a generally "C"-shaped housing 20 that preferably encircles at least 180° and includes an opening 30 sized to permit housing 20 to pass around the neck 40 of a user. In the preferred embodiment, housing 20 is formed of a plastic material and comprises a central housing portion 50-A and end portions 50-B, the portions being joined together by flexible linkages 60, that may be accordion or bellows-like in function. Collectively, portions 50-A and 50-B are biased by linkages 60, and/or by the material comprising housing 20 to urge cooler 10 to fit snugly but comfortably around the user's neck. Of course housing 20 should be sufficiently flexible and/or articulatable to permit easy removal of device 10 from a user's neck. Those skilled in the art will appreciate that more or fewer than two linkages 60 could be employed, and that if a suitably elastic housing material were used, possibly no linkages would be required. Preferably distal ends 70 of housing portions 50-B are rounded to promote user comfort in wearing cooler 10. (Obviously, a forehead cooler 10' will be sized to fit comfortably about the forehead of a user.) Preferably central housing portion 50-A includes a motor housing 80 having air intake vents 90, and a small DC motor 100 retained within a retainer cup 102 within housing 80. A battery 110 (e.g., a 1.5 VDC AA unit) is retained within a battery compartment 120 that may be formed on an adjacent region of housing 20. A user-accessible ON/OFF switch 130 enables the user to activate motor 100 by switcheably connecting/disconnecting battery 110 from the motor. (As shown in FIG. 2, when activated, motor 100 rotates a fan blade assembly 200.) Of course DC motor 100 may be powered by other than a battery. For example, solar cells might be disposed on the exterior surface of device 10 to generate motor operating potential. Alternatively, motor 100 might be a mechanical, wind-up type motor that requires no electrical operating potential.

Referring again to FIG. 1, preferably housing portions 50-A, 50-B include liquid intake or input slot openings 140 in their exterior surface, e.g., the housing surface that does not face toward the user's neck. Of course more or fewer slots can be provided than the number shown, and the shape of some or all of the slots may differ from what is depicted in FIG. 1. Preferably the upper and lower surfaces of the housing portions also include a plurality of air exit vent openings 150, to promote cooling. It is understood that the shape, number and location of vent openings 150 may differ from what is shown in FIG. 1. For example, substantially more such openings may be provided.

As best seen in FIGS. 1 and 2, cooler 10 further includes water (or liquid) retaining or absorbing material, preferably foam-like porous sponge material 160, that is disposed within housing 20 adjacent the inner wall of the housing exterior surface. When device 10 is used material 160 is saturated with liquid, preferably water, introduced via slots 140. Preferably material 160 is ordinary cellulose sponge, a material that can absorb water to saturation, and then retain the water without undue expulsion, e.g., by leaking out of housing 20 onto the user. Of course other materials with similar water retaining characteristics may be used for material 160. Experiments by applicant with open cell high density polyethylene foam including HDPE and PVA sponge indicate that while such material adequately retains water, water migration through the material is slower than if cellulose sponge material were used. However, material 160 need not necessarily be foam-like or spongy, and could instead be a fabric, or a non-woven material.

Cooler 10 also includes a heat dissipating member 170 that preferably is metal. Heat dissipating member 170 is retained by holder 20 such that the first dissipator surface 172 is urged against the neck of the user (see FIG. 2). Surface 172 draws body heat from the user's neck into the dissipator member 170. In the embodiment of FIG. 1, there is a single heat dissipating member 170 for each housing portion. However, a plurality of smaller heat dissipating members 170 may be provided in each housing portion as shown in FIG. 2, especially if the housing portions are sufficiently flexible.

As will be described, water-saturated sponge material 160 within housing 20 wets plenum-facing second surface 174 of member 170. An evaporation is promoted that lowers the temperature of surface 172, thus cooling the user's neck.

Figure 3:
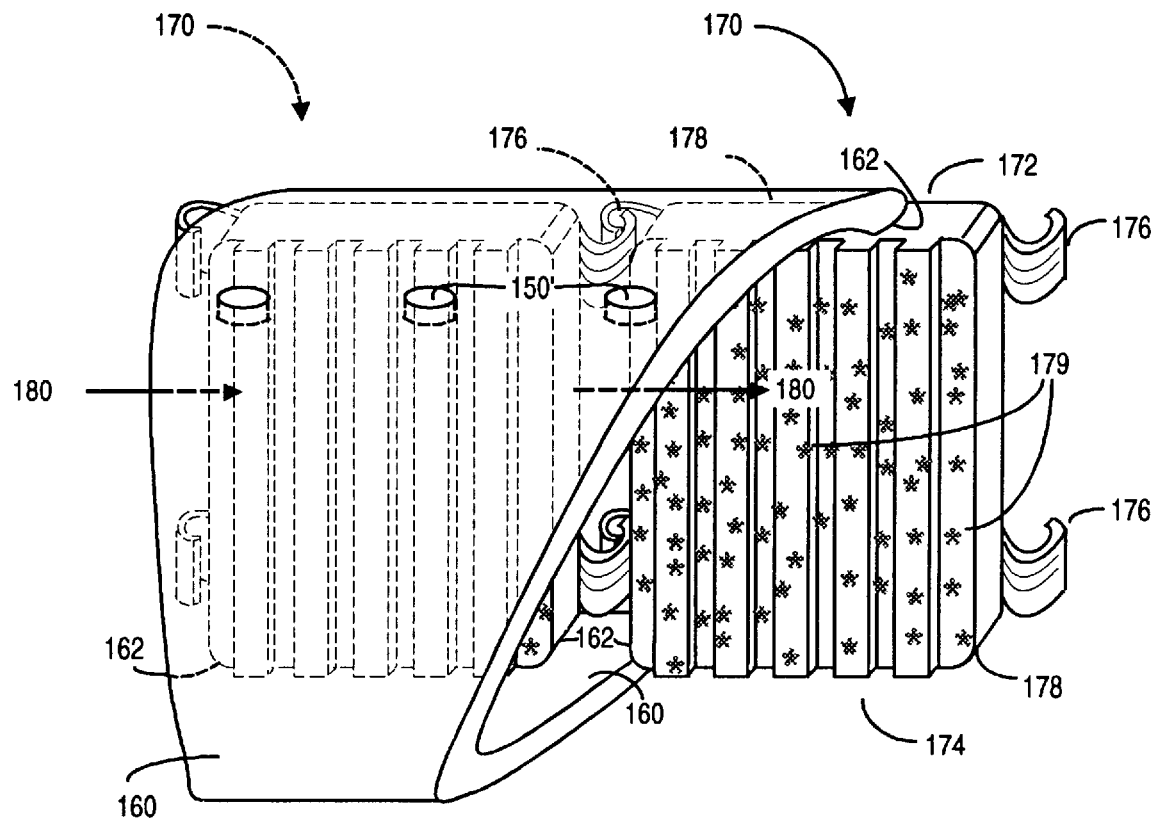
FIG. 3 is a perspective partial cutaway view depicting the plenum-facing side of the dissipator plates and sponge material and the resultant plenum, according to the present invention.

In the embodiments of FIGS. 2 and 3, the dissipating member comprises a plurality of aluminum plates or elements 170, joined vertical edge-to-vertical edge by mechanisms 176. Mechanisms 176 preferably are biased hinges that urge plates 170 to flexibly conform to the surface of the user's neck. Although mechanisms 176 are depicted in FIG. 3 as being hinge-like, other mechanisms that retain adjacent plates 170 while urging the plates to generally conform to the shape of a user's neck may be used instead. For example, mechanisms 176 could include hinges (including plastic flexible tape as hinges) that include a torsion spring to create a bias force. Mechanisms 176 might include a band of metal that creates a bias force, using either a separate band between adjacent plates 170, or one band to connect and bias many or indeed all of the plates 170.

Thus, it will be appreciated that heat dissipator member 170 might itself comprise a continuous band of flexible conductive material, or a separate such band for each housing portion (e.g., as shown in FIG. 1), rather than the plurality of plates depicted in FIG. 2. In such an implementation, there might be no need for separate bias or joining mechanisms 176. Regardless of the implementation, material 170 should be a good dissipator of heat, preferably be lightweight, and should be biased to conform generally and flexibly to the user's neck.

As best seen in FIGS. 2 and 3, portions of sponge material 160 preferably contact the upper and/or lower regions 178 of dissipator plates 170. However, exterior plate surface 174 is spaced-apart from material 160 such that plenums 180 are defined within housing 20. As will be described, fan 100 and fan blade assembly 200 move ambient air into housing 20 and along plenums 180 to promote evaporative cooling of the user's neck. FIG. 2 is intended to show the relative relationship of the components comprising device 10, and is not drawn strictly to scale. In practice plenums 180 may be larger than what is shown to promote more efficient cooling. As noted, sponge material 160 is preferably saturated with water. To minimize loss of water through evaporation (other than at region(s) 178 of the dissipator plates), the outer surface or skin of material 160 preferably is coated or covered with a thin moisture barrier, a plastic film, for example. However, as shown in FIG. 3, at the interface 162 of the sponge material and dissipator plates regions 162 the barrier is not formed, (or if formed is removed) to promote water cooling of dissipator plates 170. Preferably such moisture barrier on material 160 is not formed (or removed if formed) adjacent slits 140 in housing 20, to facilitate loading the sponge material with water. The moisture barrier not only prevents air circulating in plenums 180 from evaporating water from the sponge material, but also reduces leakage of water onto the user's neck or clothing. Moisture loss may also be reduced by providing slots 140 with covers that are removed or hinged out of the way when adding water to cooler 10, but are otherwise closed. Note the presence of openings 150', which coincide in location with openings 150 in the upper and lower housing surfaces. Openings 150' may be larger than openings 150 but should not be smaller, to avoid impeding the air flow exiting the device housing.

The preferably somewhat flexible nature of housing 20 and material 60 is such that the dissipator plates 170 are urged towards the user's neck to make reasonably good thermal contact therewith. Heat from the user's neck is transferred at least in part to surface 172 of plates 170, which plates are cooled by the presence of water within sponge material 160.

To promote water-cooling of plates 170, a water wicking action is encouraged along plenum-facing surface 174 of dissipator plates 170. As seen in FIGS. 2 and 3, surface 174 preferably includes fins, projecting pins or rectangles or squares, or the like to increase surface area. It is understood that the configuration shown in FIGS. 2 and 3 is only exemplary, and that the drawings are not precisely scaled. In practice, a surface 174 having projecting pins rather than fins appears to promote more efficient heat transfer and cooling. In such an embodiment, heat transfer efficiency is promoted by forming dissipator plates 170 with many relatively thin, preferably pin-shaped, projections on plenum-facing side 174.

To promote migration of water from the sponge material into surface 174, a wicking material 179 is provided. Wicking material 179 preferably comprises silicon carbide powder, about 100 mesh, although 80 mesh aluminum powder may be used, among other wicking materials. A thin layer of glue is applied at least to regions of surface 174 of plates 170, and the wicking powder is dusted onto the glued regions. Applicant used commercially available Gorilla brand premium glue although other adhesives could be used. The plate with glued powder is then dried, e.g., for about 30 minutes at about 300° F. Alternatively, the heat dissipator plates could be flocked with a short fiber material, although applicant has experienced some inconsistency in temperature drops using various flocked coatings. As yet another alternative, surface 174 might be acid-etched or sandblasted to define a wicking surface, without using mesh powders and adhesives, or flocking material.

To further promote wicking and resultant cooling efficiency, a surfactant, e.g., household liquid dishwashing detergent, is applied to the wicking-coated surfaces of plates 170 during device manufacture. Preferably, sponge material 160 is soaked with the same surfactant during manufacture as well. It is anticipated that users will on occasion re-apply surfactant to the metal plates and sponge material, when cooling efficiency appears to have degraded.

Figure 4:
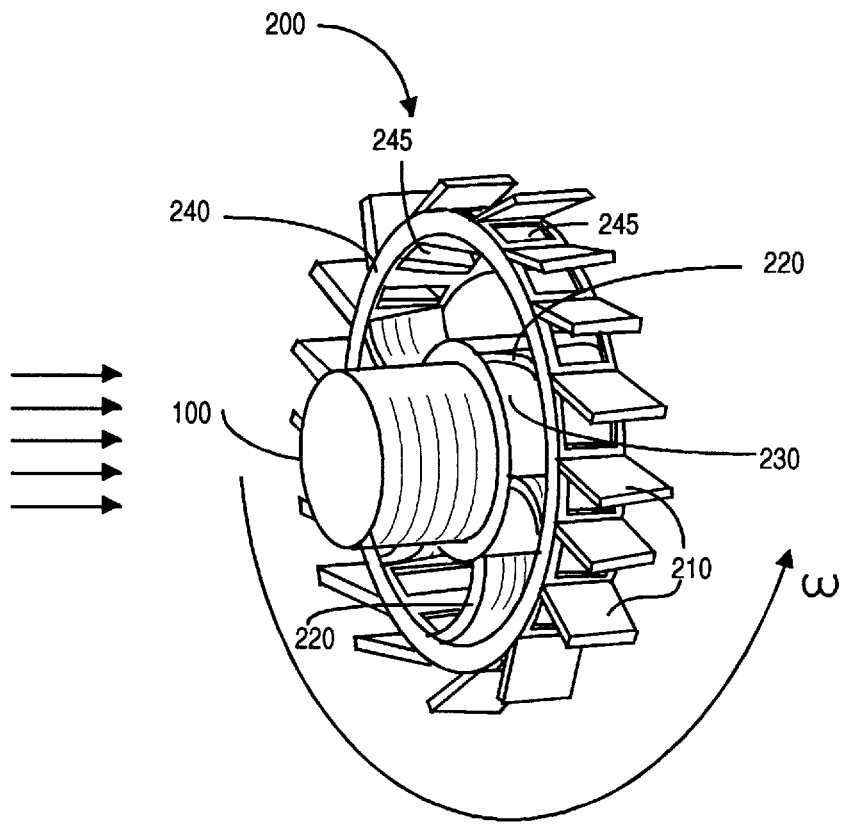
FIG. 4 is a perspective view of a motor and a preferred fan blade assembly, according to the present invention.

In using device 10, material 160 is saturated with water via openings 140. The evaporative neck cooler is then put around the user's neck (or forehead) and switch 130 turned ON. As battery 110 energizes motor 100, fan blade 200 rotates. As seen in FIG. 4, fan blade 200 preferably includes a radially configured outer blade portion 210, and an inner axially configured blade portion 220. Inner blade portion 220 is formed on a hub 230, and a second hub 240 is common to blade portions 210 and 220. Alternatively, fan blade 200 may comprise only axially disposed blades, or only radially disposed blades set at an angle that forces a portion of the air toward the underlying heat dissipator surface and a portion of the air outward toward the end sections of the housing. In any event, second hub 240 preferably includes openings 245 to permit air passage therethrough. Alternatively, second hub 240 may be fabricated as a pair of spaced-apart hoops that are spanned and joined by fins 210 on the exterior surface.

In FIG. 4, the direction of air flow is left-to-right, as shown by the parallel arrows on the left, and the rotational direction is as shown by the curved arrow ω. The inner axial blades 220 draw ambient air through fan housing vents 90 (see FIG. 1) into housing 20, and the radial outer blades 210 then move or circulate this air along plenums 180. This circulated air then evaporatively cools water-moistened surface 174 of plates 170. Surface 174 will have been wetted by water from sponge material 160 that, due to the absence of a moisture barrier at interface regions 162 (see FIG. 3) can move onto surface 174, promoted by wicking material 179. The air exits the plenum via openings 150' in the sponge material, and corresponding openings 150 in the upper and lower housing surfaces.

One may first treat the sponge material with an anti-bacterial anti-fungal solution. Such a solution can inhibit growth of undesired microorganisms within the neck cooler, promoting hygienic use of the cooler.

Understandably it is important that water be retained within sponge material 160 for efficient cooling to occur. Optionally, neck cooler 10 can be provided with a visual indicator 250 (see FIG. 1) to provide visual indication when material 160 is becoming dry. For example, material 250 may be a strip of thin water permeable material, cloth for example, impregnated with cobaltous chloride. This chemical will cause strip 250 to appear pink when wet, but blue when dry.

The present invention will provide effective cooling as long as metal plate surfaces 174 remain moist, and as long as fan 100 circulates air into and within housing 20. In practice, plate surfaces 174 can remain moist for 3 hours or more, and a typical AA battery 110 can power 100 for about 14 hours. Temperature reductions from ambient air temperature of up to about 20° F. are obtained at about 100° F. ambient and about 20% relative humidity. Even greater temperature reductions can be attained at increasing ambient temperature and/or decreasing relative humidity. These cooling reductions are attained without requiring a user to handhold a cooling device, and without exposing the user to water dripping onto the neck or clothing. While being thus cooled, the user can freely participate in all manner of indoor or outdoor activities including without limitation walking, jogging, bicycle riding, exercising, working, and motor vehicle operating.

While the present invention has been described with respect to a cooling device for a human, e.g., for use on the neck, forehead, or other body part, it will be understood that other animals may also benefit from the device. For example, a suitably sized device might be worn by pets. A guide dog for a blind person might especially benefit from a neck evaporator device on a hot day when excessive heat might otherwise impair the dog's ability to protect its owner.

It will also be appreciated that while the preferred embodiment has been described with respect to a selfretaining device, e.g., a "C"-shaped device that supports itself, the present invention could be fabricated as a flat device that is strapped or otherwise supported against a surface to be cooled. For example, a flat-shaped device according to the present invention could be strapped to a user's chest, back or other body region to promote cooling for comfort or perhaps for medical purposes.

Modifications and variations may be made to the disclosed embodiments without departing from the subject and spirit of the invention as defined by the following claims.

What is claimed is:

1. A device for cooling a body portion of a user, comprising:

a generally C-shaped housing sized to fit around at least 180° conformally about said body portion;

a heat dissipating member disposed within said housing such that a first surface is biasedly urged against said body portion, wherein said heat dissipating member has the first surface facing said body portion and an opposite second surface having a greater surface area than said first surface to promote heat dissipation;

a liquid-retainable material disposed within said housing so as to contact at least a chosen one of an upper region and a lower region of said heat dissipating member while being spaced-apart from said second surface of said heat dissipating member to define at least one plenum; and means for moving ambient air into said housing, along said plenum, and out of said housing.

2. The device of claim 1, wherein said housing includes at least:

a central housing portion;
a first housing portion;
a second housing portion;
a first articulation that joins a first end of said central housing portion to a first end of said first housing portion; and
a second articulating that joins a second end of said central housing portion to a first end of said second housing portion.

3. The device of claim 2, wherein said heat dissipating member includes one metal plate for each portion of said housing.

4. The device of claim 1, wherein said heat dissipating member includes a plurality of metal plates;

wherein adjacent ones of said metal plates are biasedly joined together such that said metal plates are conformally urged toward said body portion of said user.

5. The device of claim 2, wherein each portion of said housing includes at least two said metal plates.

6. The device of claim 1, wherein at least a portion of said second surface is fabricated so as to promote wicking action of moisture from said liquid-retainable material onto at least a portion of said second surface.

7. The device of claim 1, wherein said liquid-retainable material has at least one characteristic selected from the group consisting of (a) said material is a foam-like porous liquid absorbing material, and (b) said material includes cellulose sponge.

8. The device of claim 1, wherein said liquid retaining material has an exterior surface everywhere covered by a moisture barrier skin except at regions whereat said liquid retaining material contacts a said region of said heat dissipating member and except at a region whereat said liquid may be introduced into said liquid retaining material.

9. The device of claim 1, further including visual means for indicating moisture content of said liquid retaining material, said visual means disposed in contact with an exterior surface of said liquid retaining material so as to be visible to a person viewing said device.

10. The device of claim 1, wherein said housing defines at least one liquid intake slot, disposed to expose a region of said liquid retaining material such that liquid may be introduced through said slot into said liquid retaining material, and further defines at least one air vent in communication with said plenum through which air may exit said housing.

11. The device of claim 1, wherein said means for moving ambient air includes an electric fan and a fan blade assembly, wherein at least said fan blade assembly is disposed within said housing.

12. The device of claim 1, wherein said means for moving ambient air includes a battery operated electric fan, and a fan blade assembly having a configuration selected from the group consisting of (a) inner axially disposed blades and concentric outer radially disposed blades, (b) inner axially disposed blades and outer axially disposed blades, and (c) inner radially disposed blades and outer radially disposed blades.

13. The device of claim 1, wherein said body portion is selected from the group consisting of a neck and a forehead.

14. A self-contained device for cooling the neck or forehead of the body of a user, comprising:

a generally C-shaped housing sized to fit around at least 180° conformally about said user's neck or forehead and defining at least one air intake opening, at least one moisture intake opening, and at least one air exit vent opening;

at least one heat dissipating metal plate disposed within said housing and having a first body-facing surface and an opposite plenum-facing second surface that defines a surface area exceeding an area of said first body-facing surface to promote heat dissipation, said plate being conformally urged toward said user's neck or forehead;

a liquid-retainable material disposed within said housing so as to contact at least a chosen one of an upper region and a lower region of said metal plates while being spaced-apart from said second surface of said metal plate so as to define at least one plenum, a portion of said liquid-retainable material being in proximity to said moisture intake opening in said housing; and a DC motor and fan blade assembly, at least said fan blade assembly being disposed within said housing to draw ambient air through said air intake opening into said housing for circulation along at least a portion of said plenum before exiting through said air exit vent.

15. The device of claim 14, wherein said at least a portion of said plenum-facing surface of said metal plate includes at least one projection so as to promote more efficient heat transfer, and wherein at least a portion of said second surface is treated with a wicking material so as to promote wicking action of moisture from said liquid-retainable material onto at least a portion of said second surface.

16. The device of claim 14, wherein said liquid-retainable material includes cellulose sponge.

17. The device of claim 14, wherein said liquid-retainable material is covered by a moisture barrier skin except at regions whereat said liquid retaining material contacts a said region of said heat dissipating member and except at a region whereat said liquid may be introduced into said liquid retaining material.

18. The device of claim 14, further including visual means for indicating moisture content of said liquid retaining material, said visual means disposed in contact with an exterior surface of said liquid retaining material so as to be visible to a person viewing said device.

19. The device of claim 14, wherein said fan blade assembly includes inner axially disposed blades and concentric outer radially disposed blades.

20. A method for cooling a portion of a user's body with a self-contained device, the method comprising:
   (a) biasedly retaining a first surface of a heat dissipating member against said portion, said heat dissipating member having an opposite second surface having an area exceeding an area of said first surface;
   (b) disposing a liquid-retaining material saturated with liquid such that said material contacts at least a chosen one of an upper region and a lower region of said heat dissipating member while being spaced-apart from said second surface of said heat dissipating member to define at least one plenum, wherein liquid from said material may wet said second surface of said heat dissipating member; and
   (c) moving ambient air through said plenum to promote evaporation of said liquid from said second surface;
   wherein evaporation of said liquid from said second surface lowers temperature of said heat dissipating member below ambient temperature, thus cooling said portion of said user.

\* \* \* \* \*